US006992565B1

(12) United States Patent
Giesler

(10) Patent No.: US 6,992,565 B1
(45) Date of Patent: Jan. 31, 2006

(54) ELECTRONIC COMMUNICATIONS SYSTEM

(75) Inventor: Thomas Giesler, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/554,378

(22) PCT Filed: Sep. 9, 1999

(86) PCT No.: PCT/EP99/06696

§ 371 (c)(1),
(2), (4) Date: May 12, 2000

(87) PCT Pub. No.: WO00/15931

PCT Pub. Date: Mar. 23, 2000

(30) Foreign Application Priority Data

Sep. 14, 1998 (EP) .................................. 98117343

(51) Int. Cl.
*G05B 23/00* (2006.01)
(52) U.S. Cl. ................ 340/5.72; 340/825.71; 345/156; 455/41.1
(58) Field of Classification Search ........... 340/5.72, 340/825.71; 345/156; 455/41.1
See application file for complete search history.

(56) References Cited

U.S. PATENT DOCUMENTS 4,591,854 A * 5/1986 Robinson ............... 340/825.31
5,790,043 A * 8/1998 Hettich et al. .......... 340/825.31
5,914,701 A * 6/1999 Gersheneld et al. ......... 345/156
5,973,611 A * 10/1999 Kulha et al. ............... 340/5.62

FOREIGN PATENT DOCUMENTS

EP          0843425       5/1998
WO        WO9636134      11/1996

OTHER PUBLICATIONS

Dr. Stephan Schmitz et al: "Tursteher Ohne Bodyguard—Format" Elekronik, vol. 22, 1998, pp. 148-156.

* cited by examiner

*Primary Examiner*—Michael Horabik
*Assistant Examiner*—M Shimizu
(74) *Attorney, Agent, or Firm*—Adam Stroud

(57) ABSTRACT

An electronic communication system for a vehicle, including a base station which is accommodated in the vehicle and at least one portable data carrier which is arranged to exchange data signals with the base station. A first coupling link is formed at least partly by the body of a user, whose skin is not required to be in physical contact with the data carrier, so that the body of the user contactlessly conducts displacement currents from the data carrier without contacting the data carrier. This permits the user to unlock a car door, or trunk, and/or start the vehicle, without using a key or having to touch a remote control device. The data carrier can be located in a briefcase and/or purse, and the ability to access the vehicle is not comprised even though there is no physical contact between the user and the data carrier.

13 Claims, 3 Drawing Sheets

ELECTRONIC COMMUNICATIONS SYSTEM

BACKGROUND OF THE INVENTION

1. Field of the Invention

The invention relates to an electronic communication system for a vehicle, including a base station which is accommodated in the vehicle and at least one portable data carrier which is arranged to exchange data signals with the base station.

2. Description of the Related Art

Communication systems of this kind serve notably for controlling the entry to the vehicle. Systems of the kind set forth are known as "keyless central locking systems" or "keyless go-inhibit systems". Such a system is described in the article "Türsteher ohne Bodyguard-Format" by Dr. Stephan Schmitz and Jasek Kruppa, published in the magazine "Elektronik", Vol. 22, 1998, pp. 148 to 156.

The cited publication discloses a keyless central locking system for use in vehicles which includes the following components:

a transponder which can be embedded in a chip card or in a key grip and may be provided with an antenna coil, a battery, a UHF transmitter and pushbuttons, an LF antenna in the mirror on the driver's door, an UHF receiver in the vehicle which is activated as soon as it receives (deliberately triggered by the user) an appropriate UHF sequence from the transponder, a mechanical switch in the door handle for activating a passive entry system, including an additional pushbutton for initiating the locking procedure, the base station or the door module and a control device.

The transponder transmits data signals to the vehicle via a UHF link, whereas the transmission from the vehicle to the transponder always takes place via an LF signal of a frequency of 125 kHz. If desired, the transmission from the transponder to a vehicle can also be realized by means of such an LF signal.

A keyless locking system of this kind is capable of simplifying the opening of a vehicle to some extent in comparison with the use of a mechanical door key. However, such simplification is limited by the fact that the user must still find and operate the transponder as before. Thus, the problem remains that the transponder must always be carried in a pocket or the like and that it must be retrieved therefrom in order to operate it. It is also to be noted that even this minor advantage is not achieved for the go-inhibit function, i.e. for the starting of the vehicle.

SUMMARY OF THE INVENTION

It is an object of the invention to provide an electronic communication system which allows for very simple operation in a wide variety of circumstances.

This object is achieved in an electronic communication system of the kind set forth in that the data carrier includes a first and a second electrode as well as a first data signal processing circuit which is arranged to receive and/or transmit the data signals from and to the base station, respectively, the data signals being formed by a voltage between the first and the second electrode, the base station includes at least a third and a fourth electrode as well as a second data signal processing circuit which is arranged to receive and/or transmit the data signals from and to the data carrier (carriers), respectively, the data signals being formed by a voltage between the third and the fourth electrode, during operation, the second and the third electrode are coupled to one another via a first coupling link for the transmission of the data signals, during operation the first electrode is coupled to electrical ground of the vehicle via a second coupling link for the transmission of the data signals, the fourth electrode is electrically connected to electrical ground of the vehicle, and the first and the second coupling link include at least a respective capacitive connection via an electrical field.

The communication system according to the invention enables not only very simple operation but a very high degree of reliability in a wide variety of circumstances, notably a high degree of protection against unauthorized entry. This is achieved notably in that the coupling links constructed in conformity with the invention have a range which is limited to the minimum value required for user-friendly operation, so that unauthorized entry by non-authorized third parties is precluded. This is achieved notably by the capacitive connections. Moreover, the communication system according to the invention is constructed to be variable in such a manner that it can be simply used for a variety of applications and types of operation. Specifically, it makes no difference whether operation takes place outside or inside the vehicle.

The first coupling link in a preferred embodiment of the communication system according to the invention is formed at least partly by the body of a user which conducts displacement currents. This offers the advantage that a coupling link of this kind can be implemented so as to be very well protected against tapping. Moreover, this constitutes a particularly simple implementation and operation of the communication system. The second coupling link in a further embodiment of the invention is formed at least partly by the ground. In the case of a land vehicle this is the ground or the pavement. In the case of a water vehicle, the second coupling link may also be formed at least partly by the water. This embodiment also simplifies the communication system; more specifically, the ground will invariably form a link between the vehicle and a user who is outside the vehicle, irrespective of the position of the vehicle.

Preferably, the communication system according to the invention includes at least an additional data and/or energy transmission link which involves an essentially magnetic coupling between the data carrier (data carriers) and the base station. This additional facility creates a backup system which satisfies only less severe requirements in respect of operation and reliability, but offers an emergency solution in the case of failure of the described devices of the communication system according to the invention.

If desired, coupling by way of electromagnetic waves in the UHF range or by way of infrared light can be used instead of the magnetic coupling.

The invention thus offers an electronic communication system which is based on active, capacitively coupled data carriers and electrical fields preferably conducted inside the body of a user. An emergency system which is preferably realized with inductive coupling can also be integrated. This communication system enables operation of a vehicle in such a manner that the user is granted entry to the vehicle without separate activation of a key or a comparable entry control system, but merely by activation of a door handle; moreover, the user can equally simply put the vehicle into operation, for example by actuating a starter button. The electronic communication system according to the invention monitors the entry authorization and takes the necessary protective measures against unauthorized actuations. In order to achieve this object, the user need not perform any additional operations such as, for example, actuation of a remote transmitter or a mechanical key. The authorized user instead is fully automatically recognized and authorized by the communication system according to the invention. The user carries the associated, portable data carrier in or under his or her clothing or in a purse or the like. The electrodes may be formed simply as proximity fields or touch fields in the actuation elements of the vehicle, for example the door handle or an ignition button. The arrangement of such electrodes in the communication system according to the invention offers an as high as possible degree of user comfort and reliability, notably protection against unauthorized access.

It is to be noted that the document WO 96/36134 discloses a wireless system which includes a transmitter and a receiver which are coupled via a user and the ground potential of a room. The transmitter generates low-frequency signals of low power which, due to capacitive coupling, flow through the body of the user as displacement currents. The distributed ground potential of the room constitutes the return path for the current.

It is also to be noted that EP 0 843 425 A2 discloses an electronic communication apparatus which utilizes the human body as a transmission medium. This apparatus serves to encrypt and transmit data from a transmitter, preferably constructed as a card, to a receiver which is preferably included in a base station. The transmitter includes a generator for an electrical field, a data encryption device which is activated by modulation of the electrical field, and electrodes for coupling the electrical field through the human body. The receiver includes electrodes which are in physical contact with or are arranged very near to a part of the human body so as to detect an electrical field transmitted by the body. A demodulator in the receiver extracts the data from the modulated electrical field. It is also indicated that a receiver electrode may be arranged in a metallic door handle of a vehicle.

The doors should thus be automatically unlocked when the bearer of an authorized card, i.e. an authorized transmitter, touches the door handle by hand. Touching the door handle without pulling it over a given period of time, for example 15 seconds, is intended to lock all doors.

Thus, from the cited documents it is known in principle to use electrical fields for data transmission by way of displacement currents through the human body. However, these documents do not reveal how such a system should be implemented so as to achieve the cited objects.

BRIEF DESCRIPTION OF THE DRAWINGS

Embodiments of the invention are shown in the drawing and will be described in detail hereinafter. Corresponding elements in the drawings are denoted by corresponding references; in the drawings.

DETAILED DESCRIPTION OF THE PREFERRED EMBODIMENTS

Figure 1:
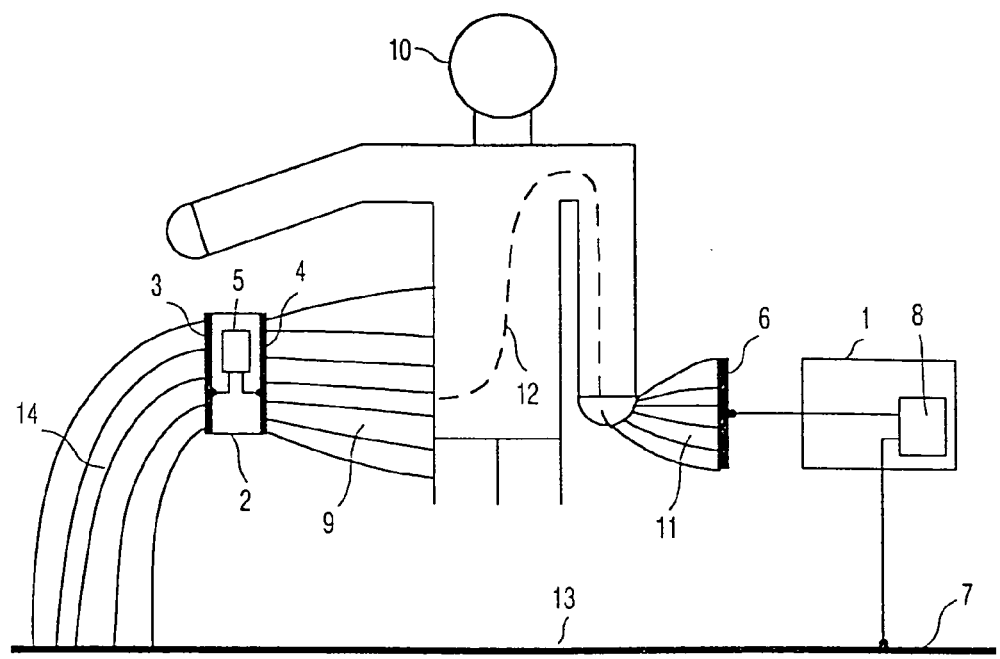
FIG. 1 is a diagrammatic representation of a first embodiment of the electronic communication system according to the invention.

FIG. 1 shows an embodiment of an electronic communication system according to the invention in which the exchange of data signals can take place at least partly via the body of a user and at the same time, or optionally, via the ground. Moreover, this embodiment of the communication system according to the invention can also be implemented without incorporating these two transmission media.

In FIG. 1, illustrating the principle and at the same time a first mode of operation of the embodiment, the electronic communication system includes a base station 1, installed in a vehicle, and at least one portable data carrier 2 which is arranged to exchange data signals with the base station 1. The data carrier 2 includes a first electrode 3 and a second electrode 4. The data carrier 2 is preferably constructed so as to be essentially flat, for example in the form of a card. The electrodes 3, 4 then cover at least partly the opposite principal surfaces of the card. A first data signal processing circuit 5, arranged to receive and/or transmit the data signals from and to the base station 1, respectively, is included in the data carrier 2. The data signals are formed by a voltage between the first electrode 3 and the second electrode 4; the data carrier 2 includes appropriate connections between the first data signal processing circuit 5 and the electrodes 3, 4.

The base station 1 includes at least a third electrode 6 and a fourth electrode 7 as well as a second data signal processing circuit 8. The second data signal processing circuit 8 is arranged to receive and/or transmit the data signals from and to the data carrier 2, respectively. The data signals are again formed by a voltage between the third electrode 6 and the fourth electrode 7; appropriate connections are provided between the second data signal processing circuit 8 and the third electrode 6 and the fourth electrode 7.

During operation of the present embodiment of the communication system according to the invention, the second electrode 4 and the third electrode 6 are coupled to one another via a first coupling link for the transmission of the data signals. In conformity with FIG. 1, the first coupling link includes a first capacitive connection 9 via an electrical field between the second electrode 4 and the body of a user 10. A second capacitive connection 11 in the first coupling link is formed via an electrical field between the body of the user 10, in this case notably the users hand, and the third electrode 6. Moreover, in conformity with FIG. 1 the first coupling link is formed at least partly by the body of the user 10 carrying displacement currents 12. The first and the second capacitive connection 9, 11 and the body of the user 10 with the displacement currents 12 conducted therein are connected in series so as to form the first coupling link.

Furthermore, in FIG. 1 the fourth electrode 7 is electrically connected to electrical ground 13 of the vehicle. During operation of the communication system shown, between electrical ground 13 and the first electrode 3 a coupling exists via a second coupling link for the transmission of the data signals. In the simplest representation of FIG. 1, the second coupling link includes a third capacitive connection 14 via an electrical field between the first electrode 3 and ground 13.

The following Figures illustrate variations and different modes of operation of the embodiment of the communication system shown in FIG. 1. The base station 1 may be connected to several electrodes, each of which itself performs the function of the third electrode 6. This means that the first coupling link may extend via each of these electrodes as desired. Preferably, these electrodes for the various operation purposes are arranged in different locations outside and inside the vehicle.

Figure 2:
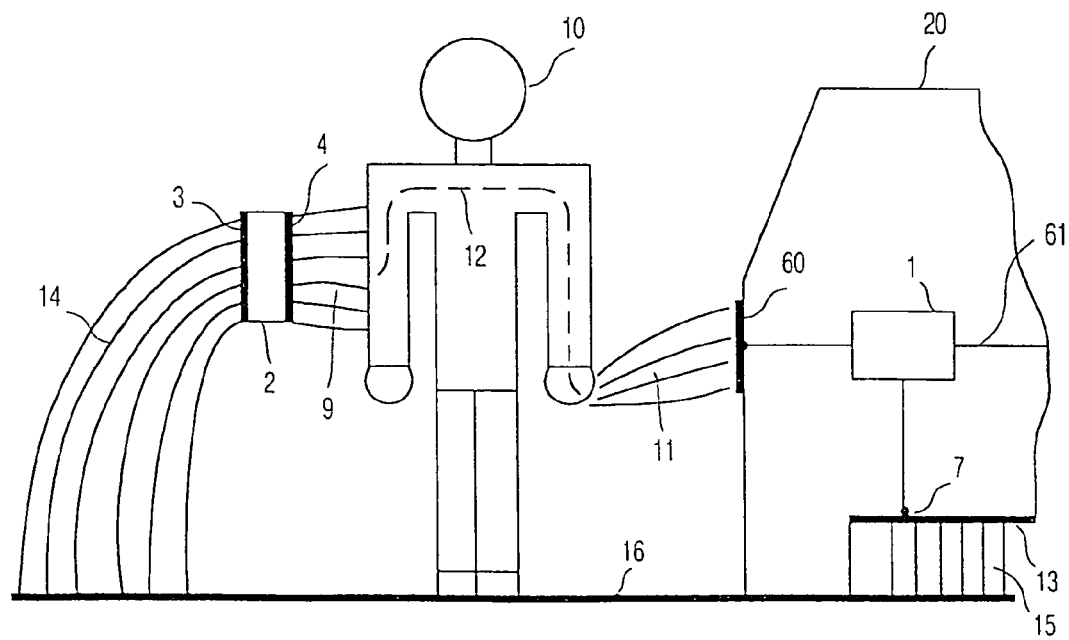
FIG. 2 shows diagrammatically a first mode of operation of the communication system of FIG. 1.

FIG. 2 shows an embodiment of the communication system according to the invention where the user 10 is outside the vehicle 20. Such a configuration of the communication system according to the invention occurs notably in controlling the entry to the vehicle, i.e. for the locking and authorized unlocking of the doors or also a trunk lid. To this end, a third electrode 60 is provided in a first mounting location on the door handle or on the actuation member for the trunk lid on the exterior of the vehicle. The connections and notably the coupling links for the transmission of the data signals are then formed as follows. The first coupling link again includes the first capacitive connection 9 between the second electrode 4 of the data carrier 2 and the body of the user 10. Via displacement currents 12 within the body of the user 10, the data signals are conducted to the hand of the user 10. The second capacitive connection 11 extends from the hand of the user 10 to the third electrode 60 on the door handle. The second coupling link as shown in FIG. 2 includes first of all the third capacitive connection 14 between the first electrode 3 of the data carrier 2 and the ground, i.e. the ground or the pavement on which the vehicle 20 rests. The ground is denoted by the reference 16. A fourth capacitive connection 15 exists between the ground 16 and the electrical ground 13 of the vehicle 20. The connection in the ground 16 preferably is realized again via displacement currents. The two capacitive connections 14, 15 and the ground, or the displacement currents flowing therein, are again connected in series in the second coupling link.

FIG. 2 shows not only the connection between the third electrode 60 and the base station 1, but also a further connection 61 which extends to a further third electrode. Instead of the further connection 61, however, a plurality of such further connections may be provided, depending on the number of third electrodes provided in or on the vehicle 20.

Figure 3:
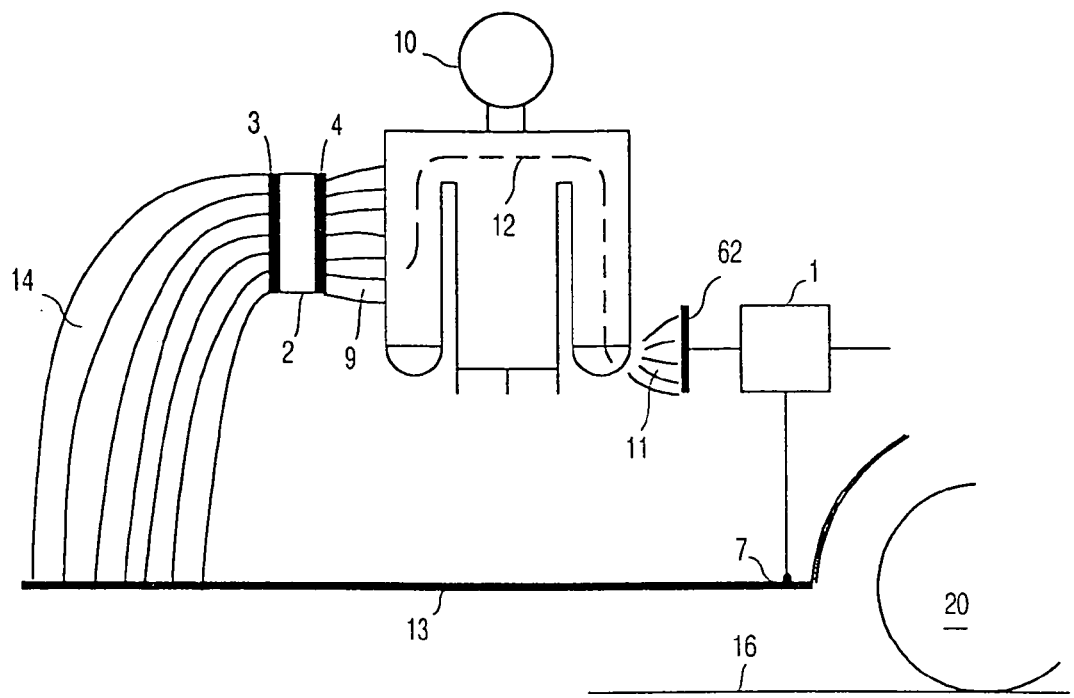
FIG. 3 shows diagrammatically a second mode of operation of the communication system shown in FIG. 1.

FIG. 3 shows a version of the embodiment of the communication system according to the invention where the user 10 sits in the vehicle. This version occurs notably when an authorized starting operation is to be carried out for the engine of the vehicle 20. In this version the first coupling link again consists of the first capacitive connection 9 and the second capacitive connection 11 as well as the displacement currents 12 in the body of the user 10. As opposed to the general illustration of FIG. 1, FIG. 3 shows the first capacitive connection 9 in a manner so as to symbolize a particularly close proximity between the user 10 and the data carrier 2, i.e. a particularly tight capacitive coupling. As will be demonstrated, however, this is not absolutely necessary for the implementation of the communication system according to the invention. The second capacitive connection 11 leads to a third electrode 62 in FIG. 3, which electrode is mounted in a second location which is preferably situated on the dashboard, notably at the area of an actuation element for the starter of the engine of the vehicle. The third electrode 62 is advantageously combined with such an actuation element for the ignition. Upon actuation by the hand of the user 10, the authorization check is then automatically performed and the engine of the vehicle 20 will be started in the case of a positive result.

In the embodiment shown in FIG. 3 the second coupling link consists of the third capacitive connection 14 between the first electrode 3 and ground 13 of the vehicle 20. Therefrom a direct, electrically conductive connection extends to the base station 1 via the fourth electrode 7.

Because the third electrode 60 in the location "door-handle" as well as the third electrode 62 in the location "actuation member for ignition" is connected to the base station 1, the communication system thus formed can be very simply and flexibly used for controlling the entry to the vehicle 20 as well as for authorizing the starting operation. The communication system can thus be used for passive entry control as well as for passive motion control, i.e. as a go inhibitor. Operation is very simple, because the user 10 need only touch the door handle and the actuation member for the ignition. Separate actuation, for example by means of a key, is dispensed with. As a result of the mounting of the third electrodes 60 and 62 and the carrying of the data carrier 2, the operations required for the data exchange are automatically performed, i.e. the transmission of the necessary data signals for the authorization checks, without intervention by the user 10. A non-authorized user is thus reliably prevented from carrying out these functions. Due to the capacitive coupling, moreover, the range of the data transmission in the communication system according to the invention is limited to the bare minimum, so that a non-authorized third party cannot tap the exchange of data signals between the data carrier 2 and the base station 1.

The data carrier 2 in the embodiments shown is preferably represented as a card-like element. However, the data carrier 2 may also be formed as a key ring, a wrist watch, a watchband or a part thereof. Furthermore, any other construction is also feasible, for example as a clothing label or the like.

The communication system according to the invention also enables identification of the position of the user 10 without requiring additional means. This identification is very simply possible via the configuration of the coupling links via the various mounting locations of the third electrodes 60, 62. This identification also serves for the operating reliability of the communication system. For example, should the user 10 with the data carrier 2 be present outside the vehicle 20, it can be prevented with certainty that a second, non-authorized person, for example a child, in the vehicle 20 can perform successful actuation of the control elements of the vehicle 20 in as far as these elements are taken up in the entry control by the communication system according to the invention. It is notably impossible for such a person to actuate the actuation element for the ignition. In another case the invention can also simply prevent the vehicle 20 from being locked from the outside by a non-authorized user for as long as the authorized user 10 sits in the vehicle.

The identification as to which of the third electrodes 60, 62 is to trigger an actuation operation can be realized simply by detecting that electrode via which the data transmission is initiated, i.e. detecting where the capacitive connection is established. Moreover, a logic combination can be formed with said actuation elements for the door handle or the ignition, supplying the base station 1 with corresponding information. As a result of such a logic combination, conversely, all third electrodes not selected at the relevant instant can be deactivated. The operator of the user 10 can thus always be exactly defined. In order to detect via which third electrode the data exchange should take place, the base station 1 can also cyclically interrogate all third electrodes for the presence of a data signal, i.e. an electrical field or a capacitive connection. In the case of a positive interrogation result, the data exchange for the entry or authorization check is then automatically started.

The third electrodes 60, 62 are preferably constructed as actuation members which are electrically insulated from the vehicle 20. If this is not desirable or impossible from a construction point of view, such actuation members can be provided with electrically insulated electrode pads. For example, such electrode pads can be mounted on or underneath the door handles. For example, mounting underneath the door handle at the same time offers protection against the weather.

Mounting such electrodes in the windows of the vehicle 20 or within a rearview mirror may also be advantageous.

As opposed to these embodiments which are advantageous for controlling the entry to the vehicle 20, the third go-inhibit electrode 62 inside the vehicle 20 is mounted preferably directly on the actuation member for the ignition, for example on the surface of a pushbutton switch. A construction in the form of a key-like switch which is to be actuated by a turning motion is also possible; the third electrode 62 can then be arranged on the surface of the grip of such a switch. Such a construction could be desirable in order to preserve for the user 10 the customary actuation motion for conventionally equipped vehicles.

Alternatively, the third electrode 62 may be formed by the steering wheel or a part thereof. A combination with an appropriately constructed actuation member for the ignition is also possible. The starting procedure for the vehicle is then triggered by touching the steering wheel and at the same time actuating the ignition. The actuation of a pedal or the combined actuation of several pedals can also be used to trigger the starting procedure in combination with the touching of the third electrode 62. Moreover, the reliability of exact identification of the position of the user 10 can be enhanced by providing additional third electrodes on at least one of the pedals. In that case the entry test is performed twice in succession, i.e. the first time via the actuation member for the ignition and the second time via the pedals, or also vice versa.

The foregoing considerations also hold to the same extent when the data carrier 2 is carried close to the body of the user 10, so that the first capacitive connection 9 is always very active. In that case there are no differences in the effectiveness of the communication system in relation to the entry control function and the go-inhibit function.

These circumstances change when for various reasons the data carrier 2 is not carried close to the body of the user 10. For example, often there are no suitable pockets in women's clothing. The communication system according to the invention is conceived to be such that the data carrier can also be carried along in a handbag, a briefcase or the like, without affecting the effectiveness. However, such a briefcase should not exert a strong electrically shielding effect, for example like an aluminium case. The electrical field strengths, notably for the first capacitive connection 9, therefore, are proportioned so that error-free data transmission is ensured also when the data carrier is carried in a handbag or similar container comparatively close to the body.

Figure 4:
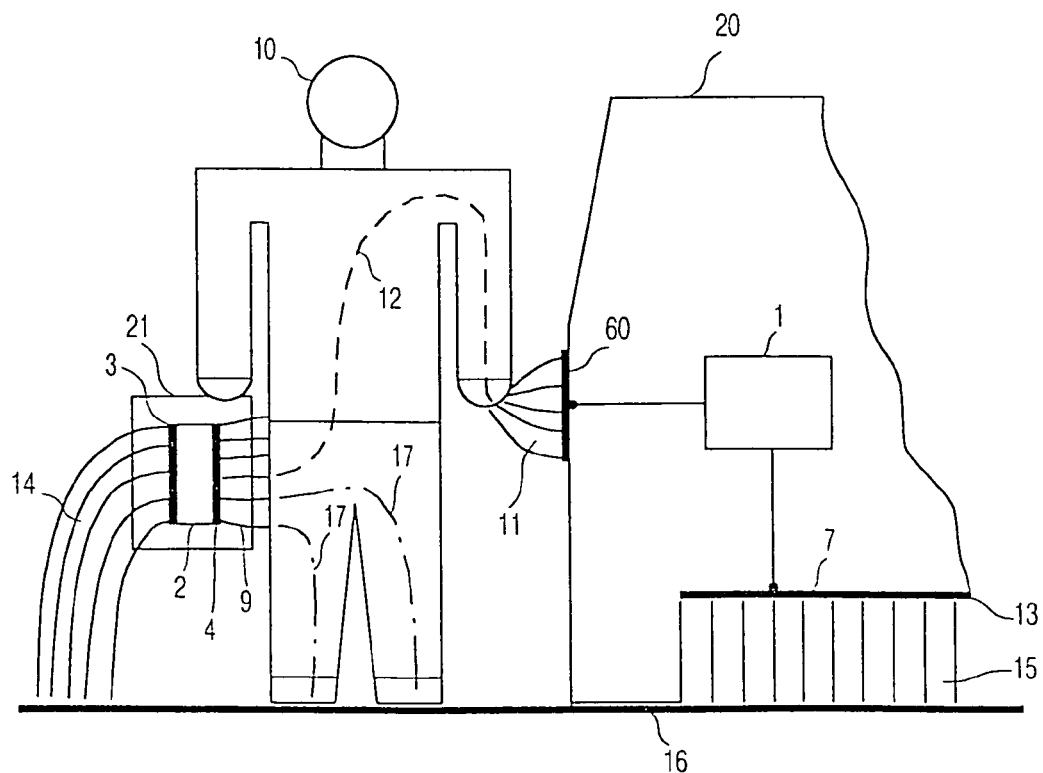
FIG. 4 shows diagrammatically a third mode of operation of the communication system shown in FIG. 1.

Such circumstances are shown, by way of example, in FIG. 4. In this case the user 10 carries the data carrier 2 in a briefcase 21. The first capacitive connection 9 then extends from the second electrode 4 to the body of the user 10 and continues therein via the displacement currents 12.

In the configuration shown in FIG. 4, however, in addition to an increased distance between the second electrode 4 and the body of the user 10 there may also occur parasitic displacement currents 17 which then flow through the legs of the user 10 to the ground 16 and establish, via said ground, a connection to the third capacitive connection 14. The members of the data carrier 2, notably the first data signal processing circuit 5, should be proportioned to ensure that these parasitic displacement currents will not endanger correct transmission of the data signals.

Figure 5:
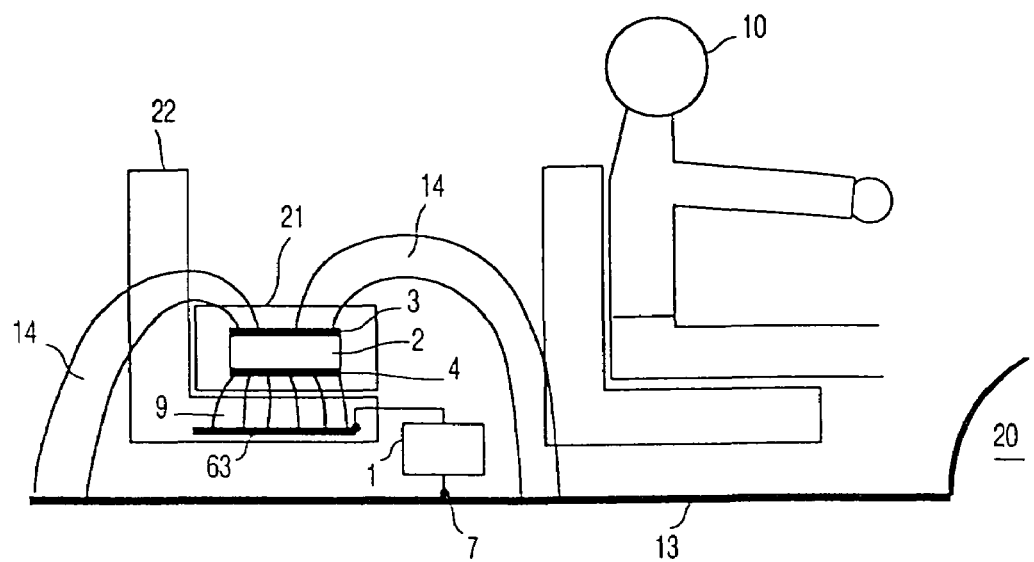
FIG. 5 shows diagrammatically a fourth mode of operation of the communication system shown in FIG. 1.

A modified configuration of the communication system according to the invention, however, arises when a data carrier which is not carried directly on the body of the user 10 is placed in the vehicle 20. It may then occur that the physical distance between the data carrier, notably the second electrode 4 thereof, and the body of the user 10 becomes too large so as to achieve correct data transmission. FIG. 5 shows such circumstances on the basis of a data carrier 2 which is stored in a briefcase 21 placed on a seat 22 of the vehicle. In that case data transmission no longer takes place via the body of the user 10. Instead further third electrodes are mounted in further locations in the vehicle. FIG. 5 shows, by way of example, a third electrode 63 mounted at the third location in the vehicle seat 22. The third electrode 63 may be formed by a metallic mesh or metal wires in the seats or by the metallic seat springs, but a seat heating by means of electrical heating wires can also be used for this purpose. The third electrode 63 is connected to the base station 1 in the same way as the third electrodes 6, 60 and 62 and can also be identified in the same way via this connection. The first coupling link in this configuration includes only the first capacitive connection 9; the second coupling link only consists of the third capacitive connection 14. The communication system according to the invention enables very reliable and simple data transmission also in this mode of operation.

Figure 6:
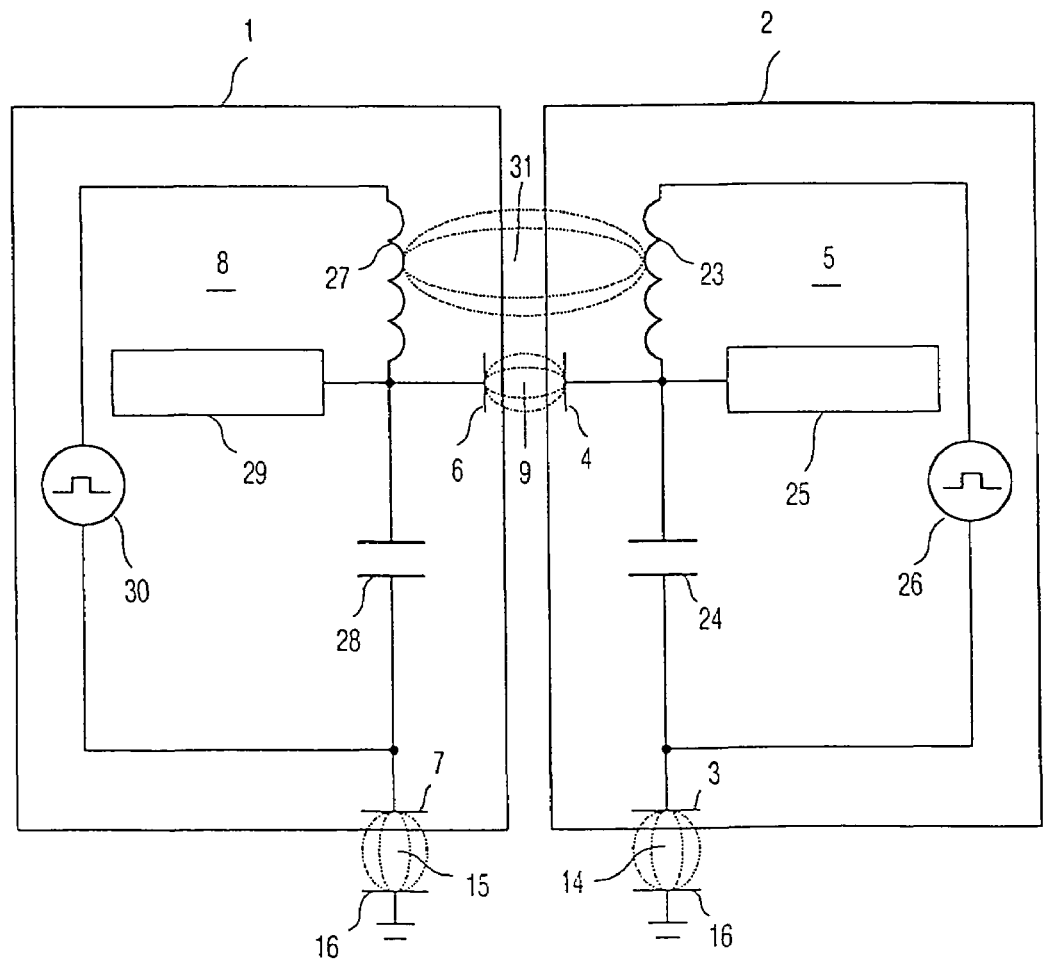
FIG. 6 shows a block diagram of an embodiment of a base station and a data carrier of the communication system shown in FIG. 1.

FIG. 6 shows an embodiment of the basic circuit construction of the data carrier 2 and the base station 1. The first data signal processing circuit 5 of the data carrier 2 in this embodiment includes a resonant circuit which includes an inductance 23 and a capacitance 24 as well as a circuit 25 with a demodulator. The circuit 25 serves to demodulate and process received data signals. There is also provided a driver circuit 26 which serves to transmit data signals. The inductance 23 and the capacitance 24 form a series resonant circuit which is connected to the driver circuit 26. Furthermore, the second electrode 4 and the circuit 25 are connected to the junction of the inductance 23 and the capacitance 24. The first electrode 3 is connected to the junction of the capacitance 24 and the driver circuit 26.

Similarly, the second data signal processing circuit 8 of the base station includes an inductance 27, a capacitance 28, a circuit 29 with a demodulator, and a driver circuit 30. These elements are interconnected in the same way as the corresponding elements of the data carrier 2. The third electrode is connected to the junction of the inductance 27 and the capacitance 28 and the fourth electrode 7 is connected to the junction of the capacitance 28 and the driver circuit 30. Whereas the first, the second, the third and the fourth electrode are cone another via the capacitive connections 9, 14, 15 in the described manner, an additional coupling exists between the inductances 23 and 27, said coupling being denoted by the reference 31. The data carrier 1 and the base station 2 can also exchange data signals via this additional, inductive coupling 31. In the receiving mode the driver circuits 26 and 30 are short-circuited and the inductances 23 and 27 form parallel resonant circuits in conjunction with the associated capacitances 24 and 28, respectively.

The described construction very simply allows for a communication system with capacitive connections in which an inductive connection is integrated. Simple means thus enable communication at option via both connections. Because the inductive connection is preferably provided only as an emergency connection, the physical dimensions of the associated inductances may be small and the inductive coupling may be proportioned in such a manner that it is effective only over very small distances. This suffices for said emergency function and enhances the security against tapping of the communication system.

The inductances for the inductive connection, also referred to as antenna coils, at the side of the base station may be provided in, for example the rearview mirror of the vehicle or in the dashboard. The communication system can then be operated via the capacitive connections as well as via the inductive connections from all desired locations. This enhances the reliability of the communication system according to the invention via an emergency function which is available on all sides, notably also in the case of unfavorable weather conditions.

The communication system according to the invention is particularly failsafe in this sense, notably also in case the power supply for the first data signal processing circuit 5 of the data carrier 2 breaks down completely. The communication system according to the invention, moreover, can also be combined with UHF or infrared data connections. This not only enhances the operating reliability because of the availability of additional emergency functions, but also enables very universal use in existing systems utilizing such data connections.

What is claimed is:

1. An electronic communication system for a vehicle, including a base station which is accommodated in the vehicle and at least one portable data carrier which is arranged to exchange data signals with the base station, wherein:
   the data carrier includes a first and a second electrode as well as a first data signal processing circuit which is arranged to receive and/or transmit the data signals from and to the base station, respectively, the data signals being formed by a voltage between the first and the second electrode,
   the base station includes at least a plurality of third electrodes and a forth electrode as well as a second data signal processing circuit which is arranged to receive and/or transmit the data signals from and to the data carrier (carriers), respectively, the data signals being formed by a voltage between the respective ones of the plurality of third and the forth electrode,
   during operation the second and one of the plurality of third electrodes are coupled to one another via a first coupling link for the transmission of the data signals,
   during operation the first electrode is coupled to electrical ground of the vehicle via a second coupling link for the transmission of data signals,
   the fourth electrode is electrically connected to electrical ground of the vehicle, and
   the first and second coupling links include at least a respective capacitive connection via an electrical field;
   wherein the first coupling link is formed at least partly by the body of the user, whose skin is not required to be in physical contact with the data carrier, so that the body of the user contactlessly conducts displacement currents from the data carrier without contacting the data carrier; and
   wherein the data carrier and the base station have a magnetic backup coupling by inductance that does not require the body of the user for operation,
   wherein the each of the plurality of third electrodes correspond to a predetermined function of the vehicle, the first coupling link requiring the second electrode to be in closer proximity with a first one of the plurality of third electrodes to actuate a first function of the vehicle than with a second one of the plurality electrodes to actuate a second function of the vehicle.

2. An electronic communication system as claimed in claim 1, characterized in that the second coupling link is formed at least partly by the ground.

3. An electronic communication system as claimed in claim 1, characterized in that it includes at least an additional data and/or energy transmission link which involves essentially magnetic coupling between the data carrier (data carriers) and the base station.

4. An electronic communication system as claimed in claim 1, characterized in that it includes at least an additional data and/or energy transmission link which involves a coupling between the data carrier (data carriers) and the base station which is formed essentially by electromagnetic waves in the UHF range.

5. An electronic communication system as claimed in claim 1, characterized in that it includes at least an additional data and/or energy transmission link which involves a coupling between the data carrier (data carriers) and the base station which is formed by infrared light.

6. A data carrier for an electronic communication system as claimed in claim 1.

7. An electronic communication system as claimed in claim 1, characterized in that the vehicle further includes a logic element that enables or disables selected ones of the functions of the vehicle depending a detected position of the user.

8. An electronic communication system for a vehicle, including a base station which is accommodated in the vehicle and at least one portable data carrier which is arranged to exchanged data signals with the base station, wherein:
   the data carrier includes a first and a second electrode as well as a first data signal processing circuit which is arranged to receive and/or transmit the data signals from and to the base station, respectively, the data signals being formed by a voltage between the first and the second electrode,
   the base station includes at least a plurality of third electrodes and a forth electrode as well as a second data signal processing circuit which is arranged to receive and/or transmit the data signals from and to the data carrier (carriers), respectively, the data signals being formed by a voltage between the respective ones of the plurality of third and the forth electrode,
   during operation the second and one of the plurality of third electrodes are coupled to one another via a first coupling link for the transmission of the data signals,
   during operation the first electrode is coupled to electrical ground of the vehicle via a second coupling link for the transmission of data signals,
   the fourth electrode is electrically connected to electrical ground of the vehicle, and
   the first and second coupling links include at least a respective capacitive connection via an electrical field;
   wherein the first coupling link is formed at least partly by the body of the user, whose skin is not required to be in physical contact with the data carrier, so that the body of the user contactlessly conducts displacement currents from the data carrier without contacting the data carrier; and wherein the data carrier and the base station have a magnetic backup coupling by inductance that does not require the body of the user for operation, wherein the each of the plurality of third electrodes correspond to a predetermined function of the vehicle, the first coupling link requiring the second electrode to be in closer proximity with a first one of the plurality of third electrodes to actuate a first function of the vehicle than with a second one of the plurality electrodes to actuate a second function of the vehicle, characterized in that the first one of the plurality of electrodes corresponds to vehicle ignition, and the second one of the plurality of electrodes corresponds to locking/unlocking doors.

9. An electronic communication system as claimed in claim 7, characterized in that the logic element disables vehicle ignition if the detected position of the user is outside the vehicle.

10. An electronic communication system as claimed in claim 8, characterized in that it includes at least an additional data and/or energy transmission link which involves essentially magnetic coupling between the data carrier (data carriers) and the base station.

11. An electronic communication system as claimed in claim 8, characterized in that it includes at least an additional data and/or energy transmission link which involves a coupling between the data carrier (data carriers) and the base station which is formed essentially by electromagnetic waves in the UHF range.

12. An electronic communication system as claimed in claim 8, characterized in that it includes at least an additional data and/or energy transmission link which involves a coupling between the data carrier (data carriers) and the base station which is formed by infrared light.

13. A data carrier for an electronic communication system as claimed in claim 8.

* * * * *